US008899014B2

(12) United States Patent
Nakano et al.

(10) Patent No.: US 8,899,014 B2
(45) Date of Patent: Dec. 2, 2014

(54) EMISSION CONTROL SYSTEM FOR INTERNAL COMBUSTION ENGINE

(71) Applicant: Denso Corporation, Kariya, Aichi-pref. (JP)

(72) Inventors: Kosuke Nakano, Toyota (JP); Shingo Nakata, Kariya (JP); Mikiyasu Matsuoka, Obu (JP)

(73) Assignee: Denso Corporation, Kariya (JP)

( * ) Notice: Subject to any disclaimer, the term of this patent is extended or adjusted under 35 U.S.C. 154(b) by 11 days.

(21) Appl. No.: 13/752,728

(22) Filed: Jan. 29, 2013

(65) Prior Publication Data

US 2013/0192210 A1 Aug. 1, 2013

(30) Foreign Application Priority Data

Feb. 1, 2012 (JP) .................................. 2012-19565
Oct. 2, 2012 (JP) ................................ 2012-220689

(51) Int. Cl.

*F01N 3/00* (2006.01)
*F01N 3/10* (2006.01)
*G01N 7/00* (2006.01)
*G01N 33/497* (2006.01)
*F02M 63/02* (2006.01)
*G01N 27/26* (2006.01)
*F01N 11/00* (2006.01)
*F02D 41/14* (2006.01)

(52) U.S. Cl.

CPC ............ *F01N 11/00* (2013.01); *F02D 41/1439* (2013.01); *F02D 41/1455* (2013.01); *F02D 41/1456* (2013.01); *F02D 41/1475* (2013.01)
USPC ................ 60/276; 60/285; 60/299; 73/23.32; 73/114.72; 123/332; 204/424; 204/427

(58) Field of Classification Search

USPC .............. 60/276, 285, 299; 73/23.32, 114.72; 123/332, 333; 204/410, 421, 424, 427
See application file for complete search history.

(56) References Cited

U.S. PATENT DOCUMENTS 4,586,476 A * 5/1986 Asayama et al. ............. 123/693

(Continued)

FOREIGN PATENT DOCUMENTS

JP 2000-054826 2/2000
JP 2011-231637 11/2011

OTHER PUBLICATIONS

Nakano, et al., U.S. Appl. No. 13/752,791, filed Jan. 29, 2013.
Office Action (3 pages) dated Jan. 20, 2014 issued in corresponding Korean Application No. 10-2013-0011211 and English translation (2 pages).

(Continued)

*Primary Examiner* — Audrey K Bradley
(74) *Attorney, Agent, or Firm* — Nixon & Vanderhye PC

(57) ABSTRACT

An emission control system for an engine includes a catalyst and an exhaust-gas sensor provided downstream of the catalyst in a flow direction of exhaust gas. The exhaust-gas sensor includes a sensor element that includes a pair of electrodes and a solid electrolyte body located between the electrodes. The emission control system further includes a constant current supply portion that changes an output characteristic of the exhaust-gas sensor by applying a constant current between the electrodes, a rich direction control portion that performs a rich direction control after a fuelling-stop control, and a characteristic control portion that performs a rich responsiveness control during the rich direction control. In the rich direction control, an air-fuel ratio of the exhaust gas is made to be richer. In the rich responsiveness control, the constant current supply portion increases a detection responsiveness of the exhaust-gas sensor with respect to rich gas.

9 Claims, 11 Drawing Sheets

(56) References Cited

U.S. PATENT DOCUMENTS

| | | | | |
|---|---|---|---|---|
| 4,741,817 | A | 5/1988 | Croset et al. | |
| 2003/0196428 | A1* | 10/2003 | Iida et al. | 60/285 |
| 2011/0192146 | A1* | 8/2011 | Sugimoto et al. | 60/276 |
| 2012/0043205 | A1 | 2/2012 | Matsuoka et al. | |
| 2013/0192211 | A1 | 8/2013 | Nakano et al. | |
| 2013/0206596 | A1 | 8/2013 | Katsurahara et al. | |

OTHER PUBLICATIONS

Office Action (2 pages) dated Apr. 28, 2014 issued in corresponding Korean Application No. 10-2013-0011211 and English translation (2 pages).

Office Action (13 pages) dated Sep. 18, 2014 issued in U.S. Appl. No. 13/761,542 to Katsurahara, filed Feb. 7, 2013.

* cited by examiner

EMISSION CONTROL SYSTEM FOR INTERNAL COMBUSTION ENGINE

CROSS REFERENCE TO RELATED APPLICATION

This application is based on and incorporates herein by reference Japanese Patent Applications No. 2012-019565 filed on Feb. 1, 2012, and No. 2012-220689 filed on Oct. 2, 2012.

TECHNICAL FIELD

The present disclosure relates to an emission control system for an internal combustion engine, which includes a catalyst used for purification of exhaust gas and an exhaust-gas sensor arranged downstream of the catalyst in a flow direction of the exhaust gas.

BACKGROUND

Conventionally, for purpose of improvement of catalytic conversion efficiency of a catalyst used for purification of exhaust gas, an emission control system for an internal combustion engine includes exhaust-gas sensors (e.g., an air/fuel sensor and an oxygen sensor) that are respectively disposed upstream and downstream of the catalyst in a flow direction of the exhaust gas. The exhaust-gas sensors detect an air-fuel ratio of the exhaust gas or detects whether the exhaust gas is rich or lean.

When the air-fuel ratio of the exhaust gas changes from rich to lean or from lean to rich, an output change of the exhaust-gas sensor, such as an oxygen sensor, may lag behind a change of an actual air-fuel ratio of the exhaust gas. Thus, the exhaust-gas sensor may have a room for improvement in detection responsiveness.

For example, as described in Patent Document 1 (JP 8-20414 corresponding to U.S. Pat. No. 4,741,817), at least one of an auxiliary electrochemical cell is incorporated to an inside of a gas sensor such as an oxygen sensor for increase in detection responsiveness.

As described in Patent Document 2 (JP 2000-054826 A), a catalyst such as a three-way catalyst used for purification of exhaust gas may possibly be in a lean state, in which an oxygen amount stored in the catalyst (i.e., an oxygen amount adsorbed in the catalyst) is relatively large, after a fuelling-stop control in which fuel injection of an internal combustion engine is stopped, i.e., after resumption of the fuel injection. Thus, a rich direction control is performed after the fuelling-stop control in an emission control device in Patent Document 2, in which an air-fuel ratio of exhaust gas is controlled to be richer. Accordingly, it can be limited that the catalyst becomes in the lean state, in other words, the oxygen amount stored in the catalyst can be reduced.

In Patent Document 1, the auxiliary electrochemical cell is necessarily incorporated to the inside of the gas sensor. Thus, when the auxiliary electrochemical cell is incorporated to a general gas sensor that does not have an auxiliary electrochemical cell, the general gas sensor may need to be changed greatly in structure. For practical use, the gas sensor may be required to be changed in design, and a manufacturing cost of the gas sensor may be increased.

The present inventors study a system that changes an output characteristic of an exhaust-gas sensor located downstream of a catalyst so as to increase responsiveness (lean responsiveness) of the exhaust-gas sensor with respect to lean gas, in order to detect a decrease of NOx conversion efficiency of the catalyst. In the emission control device in Patent Document 2, the rich direction control may be terminated when the output of the exhaust-gas sensor located downstream of the catalyst exceeds a rich threshold. In this case, if a control for increase of the lean responsiveness of the exhaust-gas sensor is performed during the rich direction control, a time point when the output of the exhaust-gas sensor exceeds the rich threshold may retard because responsiveness (rich responsiveness) of the exhaust-gas sensor with respect to rich gas is relatively low during the control for increase of the lean responsiveness. Therefore, the termination of the rich direction control may retard, and emission rate of CO, HC may be thereby increased. As a result, emission gas may be deteriorated.

It is an objective of the present disclosure to provide an emission control system for an internal combustion engine, which is capable of changing an output characteristic of an exhaust-gas sensor without great change in design and cost increase, and capable of limiting deterioration of emission gas due to a rich direction control performed after a fuelling-stop control.

SUMMARY

According to an aspect of the present disclosure, an emission control system for an internal combustion engine includes a catalyst, an exhaust-gas sensor, a constant current supply portion, a rich direction control portion and a characteristic control portion. The catalyst is used for purification of exhaust gas discharged from the engine. The exhaust-gas sensor is provided downstream of the catalyst in a flow direction of the exhaust gas to detect an air-fuel ratio of the exhaust gas or detects whether the exhaust gas is rich or lean. The exhaust-gas sensor includes a sensor element that includes a pair of electrodes and a solid electrolyte body located between the pair of electrodes. The constant current supply portion changes an output characteristic of the exhaust-gas sensor by applying a constant current between the pair of electrodes. The rich direction control portion performs a rich direction control, in which an air-fuel ratio of the exhaust gas flowing into the catalyst is made to be richer than a target air-fuel ratio set based on a normal operation condition, after a termination of a fuelling-stop control in which fuel injection of the engine is stopped. The characteristic control portion performs a rich responsiveness control, in which the constant current supply portion is controlled to increase a detection responsiveness of the exhaust-gas sensor with respect to rich gas, during the rich direction control.

Accordingly, the output characteristic of the exhaust-gas sensor can be changed by applying the constant current between the pair of electrodes. In this case, there is no need to incorporate an auxiliary electrochemical cell or the like to an inside of the exhaust-gas sensor. Therefore, the output characteristic of the exhaust-gas sensor can be changed without great design changes and cost increase. Furthermore, an emission rate of CO or HC (rich component) generated in the rich direction control after the fuelling-stop control can be reduced, and deterioration of emission gas can be limited.

BRIEF DESCRIPTION OF THE DRAWINGS

The disclosure, together with additional objectives, features and advantages thereof, will be best understood from the following description, the appended claims and the accompanying drawings, in which:

DETAILED DESCRIPTION

Figure 1:
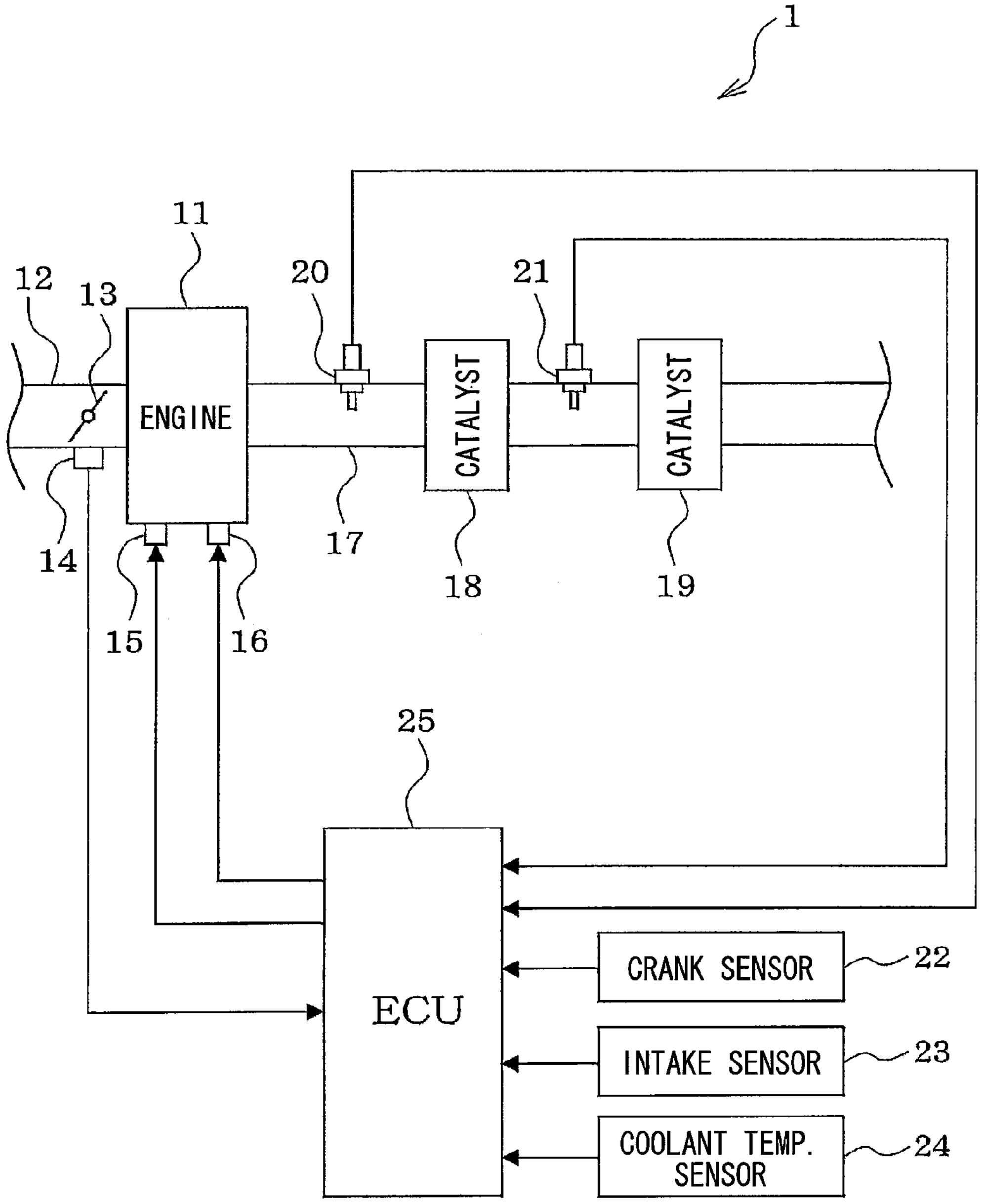
FIG. 1 is a schematic diagram showing an emission control system according to a first embodiment of the present disclosure.

Embodiments of the present disclosure will be described hereinafter referring to drawings. In the embodiments, a part that corresponds to a matter described in a preceding embodiment may be assigned with the same reference numeral, and redundant explanation for the part may be omitted. When only a part of a configuration is described in an embodiment, another preceding embodiment may be applied to the other parts of the configuration. The parts may be combined even if it is not explicitly described that the parts can be combined. The embodiments may be partially combined even if it is not explicitly described that the embodiments can be combined, provided there is no harm in the combination.

(First Embodiment)

A first embodiment of the present disclosure will be described with reference to FIGS. 1 to 9. First, an emission control system 1 of the present embodiment will be described based on FIG. 1.

The emission control system 1 includes an engine 11 (internal combustion engine), an intake pipe 12 through which intake air flows to be drawn into the engine 11, a throttle valve 13 provided in the intake pipe 12, and a throttle sensor 14 provided in the intake pipe 12. An open degree (throttle-open degree) of the throttle valve 13 is adjusted by using a motor or the like, and the throttle sensor 14 detects the throttle-open degree of the throttle valve 13. The engine 11 includes fuel injection valves 15 attached respectively to cylinders of the engine 11 to inject fuel into the cylinders or into intake ports of the cylinders, and spark plugs 16 provided in a cylinder head of the engine 11 adjacent to the cylinders respectively. The spark plugs 16 generate electric spark to ignite air/fuel mixture in the cylinders.

The emission control system 1 further includes an exhaust pipe 17 through which exhaust gas discharged from the engine 11 passes, an upstream catalyst 18 provided in the exhaust pipe 17, a downstream catalyst 19 arranged downstream of the upstream catalyst 18 in a flow direction of the exhaust gas in the exhaust pipe 17, an A/F sensor 20 (linear A/F sensor, upstream gas sensor) arranged upstream of the upstream catalyst 18 in the exhaust-gas flow direction in the exhaust pipe 17, and an oxygen sensor 21 ($O_2$ sensor, downstream gas sensor) arranged downstream of the upstream catalyst 18, i.e., between the upstream catalyst 18 and the downstream catalyst 19 in the exhaust-gas flow direction in the exhaust pipe 17. The upstream catalyst 18 and the downstream catalyst 19 are, for example, three-way catalysts that purify substances, such as carbon monoxide (CO), hydrocarbon (HC) and nitrogen oxide (NOx), contained in the exhaust gas. The A/F sensor 20 outputs a linear signal dependent on an air-fuel ratio of the exhaust gas. The oxygen sensor 21 outputs a voltage that changes depending on whether the air-fuel ratio of the exhaust gas is higher or lower than the stoichiometric air-fuel ratio, in other words, whether the air-fuel ratio is lean or rich. When the air-fuel ratio is higher than the stoichiometric air-fuel ratio, it can be said that the air-fuel ratio is lean. When the air-fuel ratio is lower than the stoichiometric air-fuel ratio, it can be said that the air-fuel ratio is rich. The oxygen gas sensor 21 may be used as an example of an exhaust-gas sensor that detects an air-fuel ratio of exhaust gas or detects whether the exhaust gas is rich or lean.

Additionally, the emission control system 1 includes various sensors that includes a crank sensor 22 that outputs a pulse signal at each predetermined rotation angle (i.e., crank angle) of a crankshaft of the engine 11, an intake sensor 23 that detects an intake air amount drawn into the engine 11, and a coolant temperature sensor 24 that detects a temperature of coolant for the engine 11. The rotation angle of the crankshaft and a rotation speed of the engine 11 are determined based on the signal outputted from the crank sensor 22.

Outputs of the above-described various sensors are input to an electronic control unit (ECU) 25. The ECU 25 includes a microcomputer 26 shown in FIG. 2, and executes a variety of engine control programs stored in a read-only memory (ROM) embedded in the microcomputer, so that the ECU 25 controls, for example, a fuel-injection amount, an ignition timing and the throttle degree (intake air amount) based on an operation state of the engine 11.

When a predetermined feedback condition is satisfied, the ECU 25 performs a main feedback control and a sub feedback control. In the main feedback control, an air-fuel ratio (fuel injection amount) is corrected based on an output of the A/F sensor 20 (upstream gas sensor) so that an air-fuel ratio of exhaust gas flowing upstream of the upstream catalyst 18 becomes a target air-fuel ratio. In the sub feedback control, the ECU 25 corrects the target air-fuel ratio based on an output from the oxygen sensor 21 (downstream gas sensor) so that an air-fuel ratio of exhaust gas flowing downstream of the upstream catalyst 18 becomes a control target value (e.g., stoichiometric air-fuel ratio), or the ECU 25 corrects a correction amount in the main feedback control or the fuel injection amount.

Next, the oxygen sensor 21 will be described based on FIG. 2. The oxygen sensor 21 includes a sensor element 31 having a cup-like shape. The sensor element 31 is accommodated in a housing or an element case, and is arranged in the exhaust pipe 17 connected to the engine 11.

Figure 2:
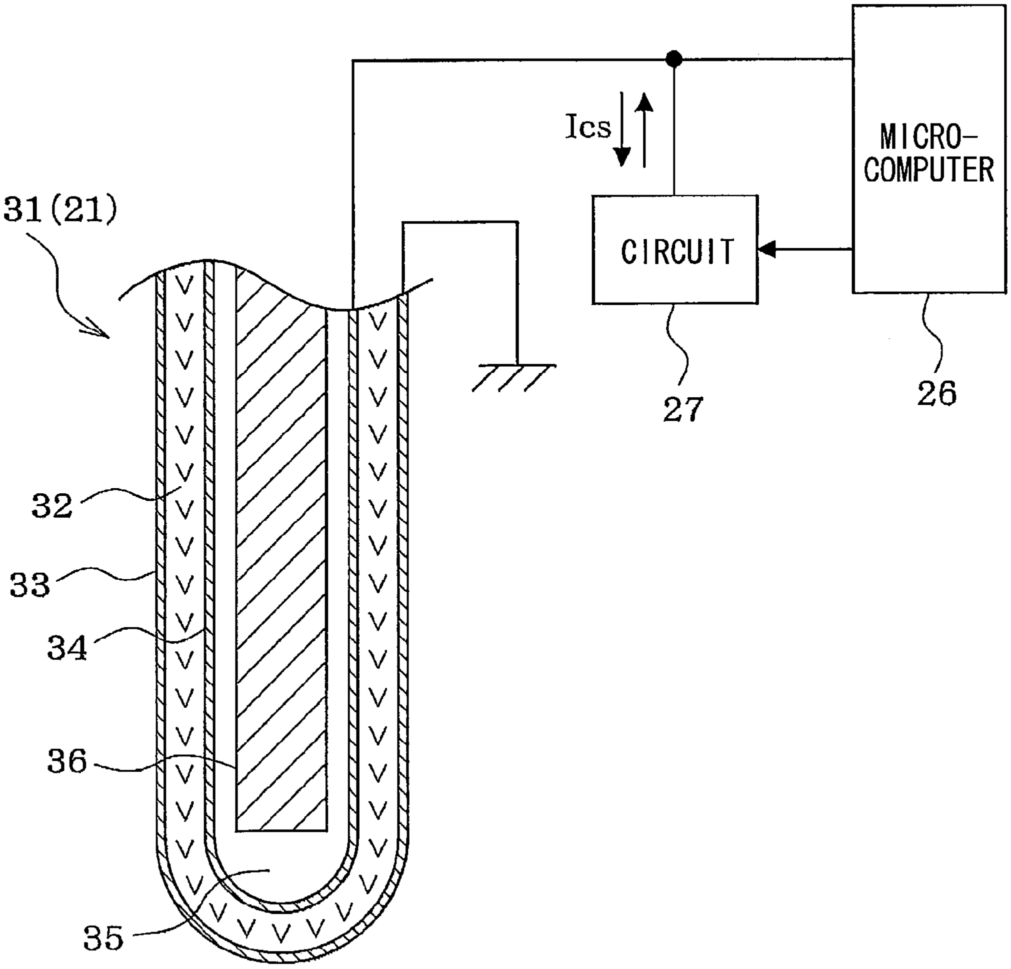
FIG. 2 is a diagram showing a sectional view of a sensor element, a constant current circuit and a microcomputer of the emission control system according to the first embodiment.

The sensor element 31 has a cup-like shape in sectional surface as shown in FIG. 2, and includes a solid electrolyte layer 32 (solid electrolyte body), an exhaust electrode layer 33 provided on an outer periphery of the solid electrolyte layer 32, and an atmosphere electrode layer 34 provided on an inner periphery of the solid electrolyte layer 32. The solid electrolyte layer 32 is made, for example, of an oxide sintered body having an oxygen-ion conductivity, and the oxide sintered body is a solid solution in which a solute, such as CaO, MgO, $Y_2O_3$ or $Yb_2O_3$, is dissolved as a stabilizing agent in a solvent, such as $ZrO_2$, $HfO_2$, $ThO_2$ or $Bi_2O_3$. The electrode layers 33 and 34 are made of noble metal superior in catalytic activity, such as platinum, and are covered with a porous material via chemical plating treatment. These electrode layers 33 and 34 are used as an example of a pair of electrodes (sensor electrodes) which are opposed to each other. The solid electrolyte layer 32 has an atmosphere space 35 surrounded by the solid electrolyte layer 32, and a heater 36 is accommodated in the atmosphere space 35. The heater 36 has a heating capacity enough to activate the sensor element 31, and the sensor element 31 is thereby heated as a whole by heat energy generated by the heater 36. An activation temperature of the oxygen sensor 21 is, for example, approximately from 350° C. to 400° C. The atmosphere space 35 introduces air therein from atmosphere so that an oxygen concentration in the atmosphere space 35 is kept at a predetermined degree.

The exhaust gas flows on outer side of the solid electrolyte layer 32 of the sensor element 31, in other words, the exhaust electrode layer 33 is exposed to the exhaust gas. The air introduced from atmosphere into the sensor element 31 is trapped on an inner side of the solid electrolyte layer 32, in other words, the atmosphere electrode layer 34 is exposed to the introduced air. Hence, an electromotive force is generated between the electrode layers 33 and 34 depending on a difference of an oxygen concentration (oxygen partial pressure) between in the exhaust gas and in the introduced air. The sensor element 31 generates an electromotive force that changes depending on whether the air-fuel ratio of the exhaust gas is rich or lean. Accordingly, the oxygen sensor 21 outputs a signal of the electromotive force dependent on the oxygen concentration (i.e., air-fuel ratio) of the exhaust gas.

Figure 3:
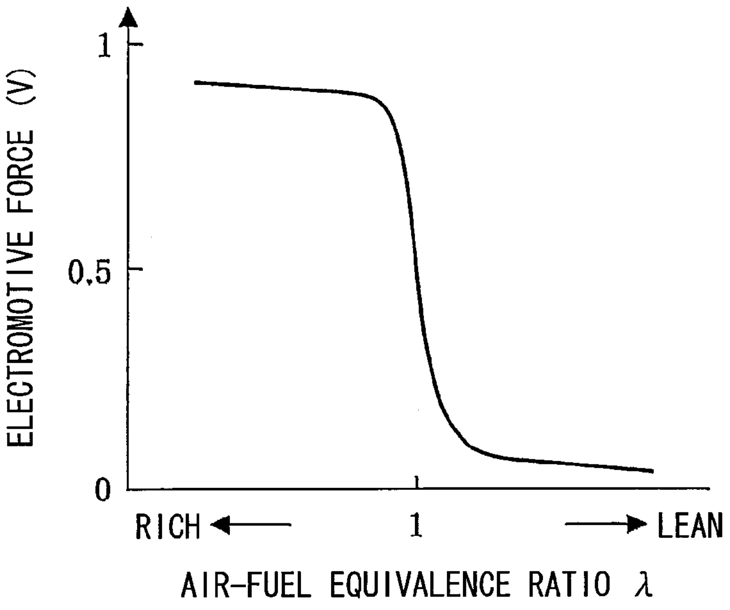
FIG. 3 is a diagram showing a relationship between an air-fuel ratio (air-fuel equivalence ratio λ) of exhaust gas and an electromotive force of the sensor element according to the first embodiment.

As shown in FIG. 3, the sensor element 31 generates an electromotive force that changes depending whether the air-fuel ratio of the exhaust gas is larger or smaller than the stoichiometric air-fuel ratio, i.e., whether the air-fuel ratio of the exhaust gas is lean or rich. Here, when the air-fuel ratio of the exhaust gas is equal to the stoichiometric air-fuel ratio, an air-fuel equivalence ratio λ is equal to 1. The sensor element 31 has a characteristic such that the electromotive force generated by the sensor element 31 changes rapidly near the stoichiometric air-fuel ratio at which the air-fuel equivalence ratio λ is equal to 1. The sensor element 31 generates a rich electromotive force when the air-fuel ratio is rich, and the sensor element 31 generates a lean electromotive force different from the rich electromotive force in voltage value when the air-fuel ratio is lean. For example, the rich electromotive force is approximately 0.9 V, and the lean electromotive force is approximately 0 V.

As shown in FIG. 2, the exhaust electrode layer 33 of the sensor element 31 is grounded, and the atmosphere electrode layer 34 is connected to the microcomputer 26. When the sensor element 31 generates an electromagnetic force depending on the air-fuel ratio (i.e., oxygen concentration) of the exhaust gas, a detection signal corresponding to the generated electromagnetic force is output to the microcomputer 26. The microcomputer 26 is, for example, provided in the ECU 25, and calculates the air-fuel ratio of the exhaust gas based on the detection signal. The microcomputer 26 may calculate a rotational speed of the engine 11 or an intake air amount based on detection results of the above-described various sensors.

When the engine 11 is operated, an actual air-fuel ratio of the exhaust gas may alternate between rich and lean repeatedly. In such case, if the oxygen sensor 21 is low in detection responsiveness, performance of the engine 11 may be affected. For example, an amount of NOx in the exhaust gas may become larger than expected in a high-load operation of the engine 11.

Figure 4A:
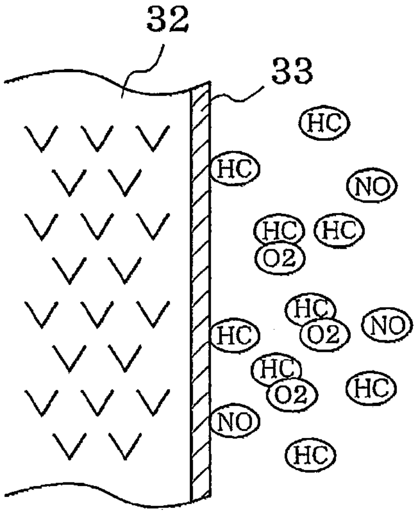
FIG. 4A is a schematic diagram showing a state of components of the exhaust gas around the sensor element when an actual air-fuel ratio changes from rich to lean, according to the first embodiment.
Figure 4B:
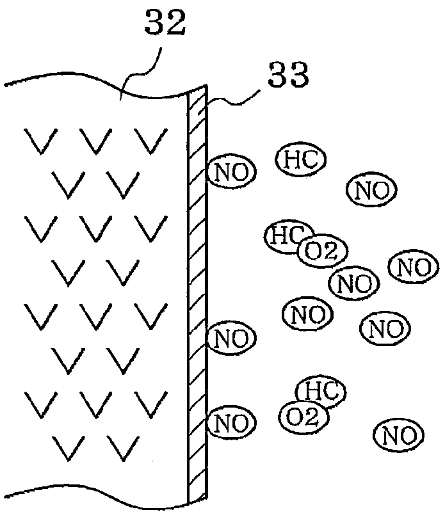
FIG. 4B is a schematic diagram showing a state of components of the exhaust gas around the sensor element when the actual air-fuel ratio changes from lean to rich, according to the first embodiment.

The detection responsiveness of the oxygen sensor 21 in a case where the actual air-fuel ratio of the exhaust gas changes from rich to lean or from lean to rich will be described. When the actual air-fuel ratio of the exhaust gas discharged from the engine 11, i.e., the actual air-fuel ratio of the exhaust gas flowing downstream of the upstream catalyst 18 changes from rich to lean or from lean to rich, component composition of the exhaust gas changes. Components of exhaust gas, which flows around the oxygen sensor 21 immediately before the change of the actual air-fuel ratio, may remain near the oxygen sensor 21 also immediately after the change of the actual air-fuel ratio. Here, the output of the oxygen sensor 21 changes in accordance with the change of the actual air-fuel ratio. Therefore, the remained components near the oxygen sensor 21 may cause the output change of the oxygen sensor 21 to retard. In other words, the detection responsiveness of the oxygen sensor 21 may decrease. Specifically, immediately after the actual air-fuel ratio changes from rich to lean as shown in FIG. 4A, a rich component such as HC remains near the exhaust electrode layer 33, and disturbs a reaction of a lean component such as NOx. As a result, detection responsiveness of the oxygen sensor 21 may decrease when the actual air-fuel ratio changes from rich to lean. Immediately after the actual air-fuel ratio changes from lean to rich as shown in FIG. 4B, the lean component such as NOx remains near the exhaust electrode layer 33, and disturbs a reaction of the rich component such as HC. Also in this case, detection responsiveness of the oxygen sensor 21 may decrease when the actual air-fuel ratio from lean to rich.

Figure 5:
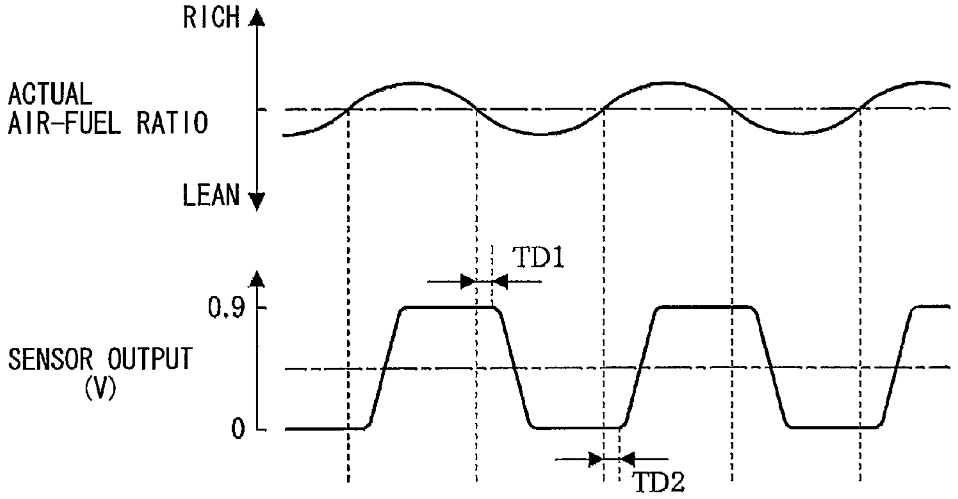
FIG. 5 is a time chart showing behavior of a sensor output in accordance with change of the actual air-fuel ratio in a case where a constant current is not applied to the sensor element, according to the first embodiment.

The output change of the oxygen sensor 21 in a case where a constant current Ics described later is not applied to the sensor element 31 will be described referring to FIG. 5. When the actual air-fuel ratio alternates between rich and lean, an output (sensor output) of the oxygen sensor 21 alternates between a rich electromotive force (e.g., 0.9 V) and a lean electromotive force (e.g., 0 V) in accordance with the alternation of the actual air-fuel ratio. In this case, the change of the sensor output lags behind the change of the actual air-fuel ratio. As shown in FIG. 5, when the actual air-fuel ratio changes from rich to lean, the sensor output of the oxygen sensor 21 changes behind the change of the actual air-fuel ratio by a time TD1. When the actual air-fuel ratio changes from lean to rich, the sensor output of the oxygen sensor 21 changes behind the change of the actual air-fuel ratio by a time TD2.

In the first embodiment, as shown in FIG. 2, a constant current circuit 27 is connected to the atmosphere electrode layer 34 to be used as an example of a constant current supply portion that supplies a constant current to the electrode layers 33 and 34. The constant current circuit 27 supplies a constant current Ics controlled by the microcomputer 26 to the pair of sensor electrodes (i.e., the exhaust electrode layer 33 and the atmosphere electrode layer 34), so that the constant current Ics flows in a predetermined direction between the pair of sensor electrodes. Accordingly, the constant current circuit 27 changes an output characteristic of the oxygen sensor 21 such that the detection responsiveness of the oxygen sensor 21 changes. The microcomputer 26 determines a flow direction and a flow amount of the constant current Ics that is to flow between the pair of sensor electrodes, and the microcomputer 26 controls the constant current circuit 27 so that the constant current Ics flows in the determined direction and amount.

The constant current circuit 27 supplies the constant current Ics in positive value or negative value to the atmosphere electrode layer 34, and is capable of adjusting the constant current Ics variably. In other words, the microcomputer 26 controls the constant current Ics variably by a pulse width modulation control (PMW control). In the constant current circuit 27, the constant current Ics is adjusted depending on a duty-cycle signal output from the microcomputer 26, and the adjusted constant current Ics is supplied to the pair of sensor electrodes to flow between the pair of sensor electrodes (i.e., the exhaust electrode layer 33 and the atmosphere electrode layer 34).

In the present embodiment, a constant current Ics flowing from the exhaust electrode layer 33 to the atmosphere electrode layer 34 is defined as a negative constant current (−Ics), and a constant current Ics flowing from the atmosphere electrode layer 34 to the exhaust electrode layer 33 is defined as a positive constant current (+Ics).

Figure 6A:
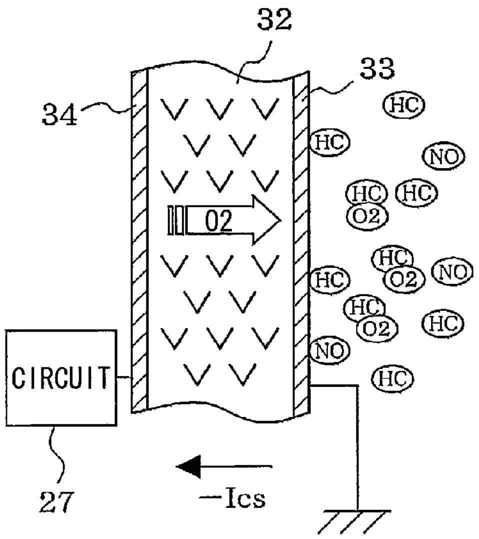
FIG. 6A is a schematic diagram showing a state of components of the exhaust gas around the sensor element when the actual air-fuel ratio changes from rich to lean, and showing a current direction in the sensor element when a lean responsiveness of the sensor element is increased, according to the first embodiment.

When the detection responsiveness of the oxygen sensor 21 is increased in a case where the actual air-fuel ratio changes from rich to lean, in other words, when a lean sensitivity of the oxygen sensor 21 is increased, the negative constant current (−Ics) is output from the constant current circuit 27 so that oxygen is supplied from the atmosphere electrode layer 34 to the exhaust electrode layer 33 through the solid electrolyte layer 32 as shown in FIG. 6A. The supply of oxygen from the atmosphere electrode layer 34 to the exhaust electrode layer 33 promotes oxidation reaction of the rich component (e.g., HC) that exists (remains) around the exhaust electrode layer 33. Hence, the rich component can be removed from around the exhaust electrode layer 33 promptly. Accordingly, the lean component (e.g., NOx) becomes to be easy to react at the exhaust electrode layer 33, and the detection responsiveness of the oxygen sensor 21 can be increased when the actual air-fuel ratio changes to rich to lean.

Figure 6B:
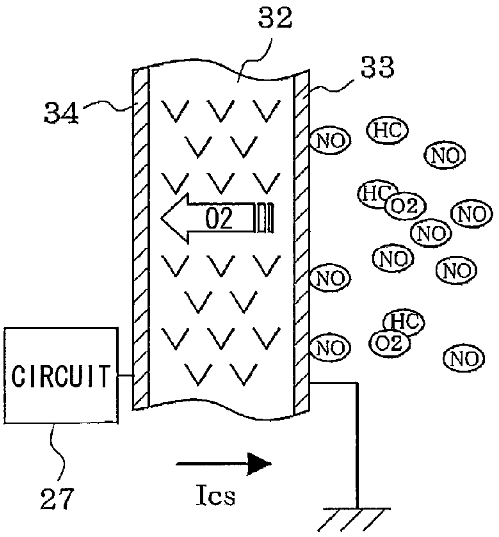
FIG. 6B is a schematic diagram showing a state of components of the exhaust gas around the sensor element when the actual air-fuel ratio changes from lean to rich, and showing a current direction in the sensor element when a rich responsiveness of the sensor element is increased, according to the first embodiment.

When the detection responsiveness of the oxygen sensor 21 is increased in a case where the actual air-fuel ratio changes from lean to rich, in other words, when a rich sensitivity of the oxygen sensor 21 is increased, the positive constant current (+Ics) is output from the constant current circuit 27 so that oxygen is supplied from the exhaust electrode layer 33 to the atmosphere electrode layer 34 through the solid electrolyte layer 32 as shown in FIG. 6B. The supply of oxygen from the exhaust electrode layer 33 to the atmosphere electrode layer 34 promotes reduction reaction of the lean component (e.g., NOx) that exists (remains) around the exhaust electrode layer 33. Hence, the lean component can be removed from around the exhaust electrode layer 33 promptly. Accordingly, the rich component (e.g., HC) becomes to be easy to react at the exhaust electrode layer 33, and the detection responsiveness of the oxygen sensor 21 can be increased when the actual air-fuel ratio changes to lean to rich.

Figure 7:
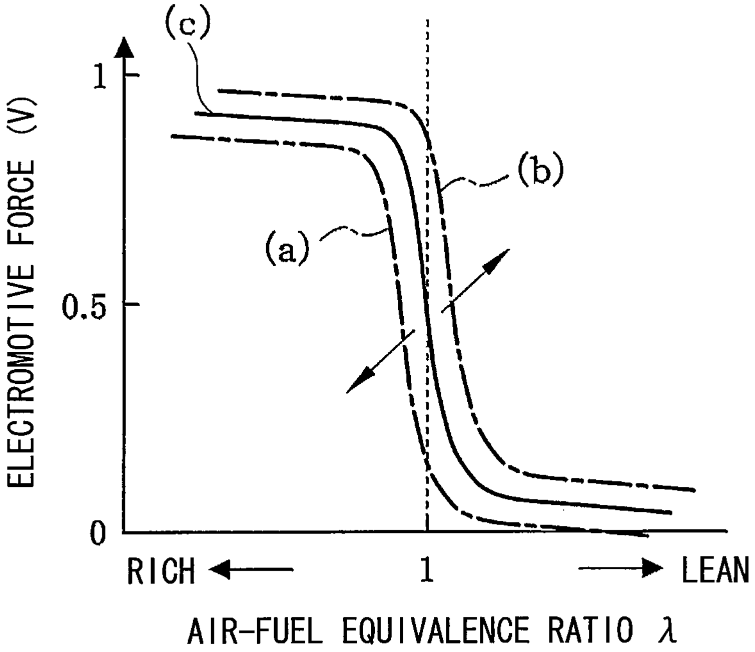
FIG. 7 is a diagram showing a relationship between the air-fuel ratio (air-fuel equivalence ratio λ) of the exhaust gas and the electromotive force of the sensor element according to the first embodiment.

FIG. 7 shows the output characteristic (electromotive force characteristic) of the oxygen sensor 21. The curve (a) shown in FIG. 7 is an output characteristic line of the oxygen sensor 21 when the detection responsiveness (lean sensitivity) is increased in a case where the actual air-fuel ratio changes from rich to lean. The curve (b) shown in FIG. 7 is an output characteristic line of the oxygen sensor 21 when the detection responsiveness (rich sensitivity) is increased in a case where the actual air-fuel ratio changes from lean to rich. The curve (c) shown in FIG. 7 is an output characteristic line same as that shown in FIG. 3.

As described above, when the detection responsiveness (lean sensitivity) is increased in the case where the actual air-fuel ratio changes from rich to lean, the negative constant current (−Ics) flows between the electrode layers 33 and 34 so that oxygen is supplied from the atmosphere electrode layer 34 to the exhaust electrode layer 33 through the solid electrolyte layer 32 as shown in FIG. 6A. Specifically, as shown in FIG. 7, the output characteristic line (a) is located on a richer side of the output characteristic line (c) in actual air-fuel ratio, and is located on a lower side of the output characteristic line (c) in electromotive force. Thus, even when the actual air-fuel ratio is within a rich region that is lower than the stoichiometric air-fuel ratio, the oxygen sensor 21 outputs the lean electromagnetic force when the actual air-fuel ratio is near the stoichiometric air-fuel ratio. Therefore, with respect to the output characteristic of the oxygen sensor 21, the detection responsiveness (lean sensitivity) of the oxygen sensor 21 is increased when the actual air-fuel ratio changes from rich to lean.

When the detection responsiveness (rich sensitivity) is increased in the case where the actual air-fuel ratio changes from lean to rich, the positive constant current (+Ics) flows between the electrode layers 33 and 34 so that oxygen is supplied from the exhaust electrode layer 33 to the atmosphere electrode layer 34 through the solid electrolyte layer 32 as shown in FIG. 6B. Specifically, as shown in FIG. 7, the output characteristic line (b) is located on a leaner side of the output characteristic line (c) in actual air-fuel ratio, and is located on a higher side of the output characteristic line (c) in electromotive force. Thus, even when the actual air-fuel ratio is within a lean region that is an air-fuel ratio region higher than the stoichiometric air-fuel ratio, the oxygen sensor 21 outputs the rich electromagnetic force when the actual air-fuel ratio is near the stoichiometric air-fuel ratio. Therefore, with respect to the output characteristic of the oxygen sensor 21, the detection responsiveness (rich sensitivity) of the oxygen sensor 21 is increased when the actual air-fuel ratio changes from lean to rich.

In the first embodiment, in order to detect a decrease of a NOx purification rate of the upstream catalyst 18 promptly, in a normal operation, a lean responsiveness control (lean RSP control) is performed, in which the constant current circuit 27 is controlled such that the lean sensitivity of the oxygen sensor 21 is increased, i.e., a lean responsiveness of the oxygen sensor 21 is increased. Specifically, the constant current circuit 27 is controlled to output the negative constant current (−Ics) such that the atmosphere electrode layer 34 supplies oxygen to the exhaust electrode layer 33. The lean responsiveness of the oxygen sensor 21 is the detection responsiveness of the oxygen sensor 21 with respect to lean gas that is exhaust gas having an actual air-fuel ratio leaner (i.e., higher) than the stoichiometric air-fuel ratio.

Figure 8:
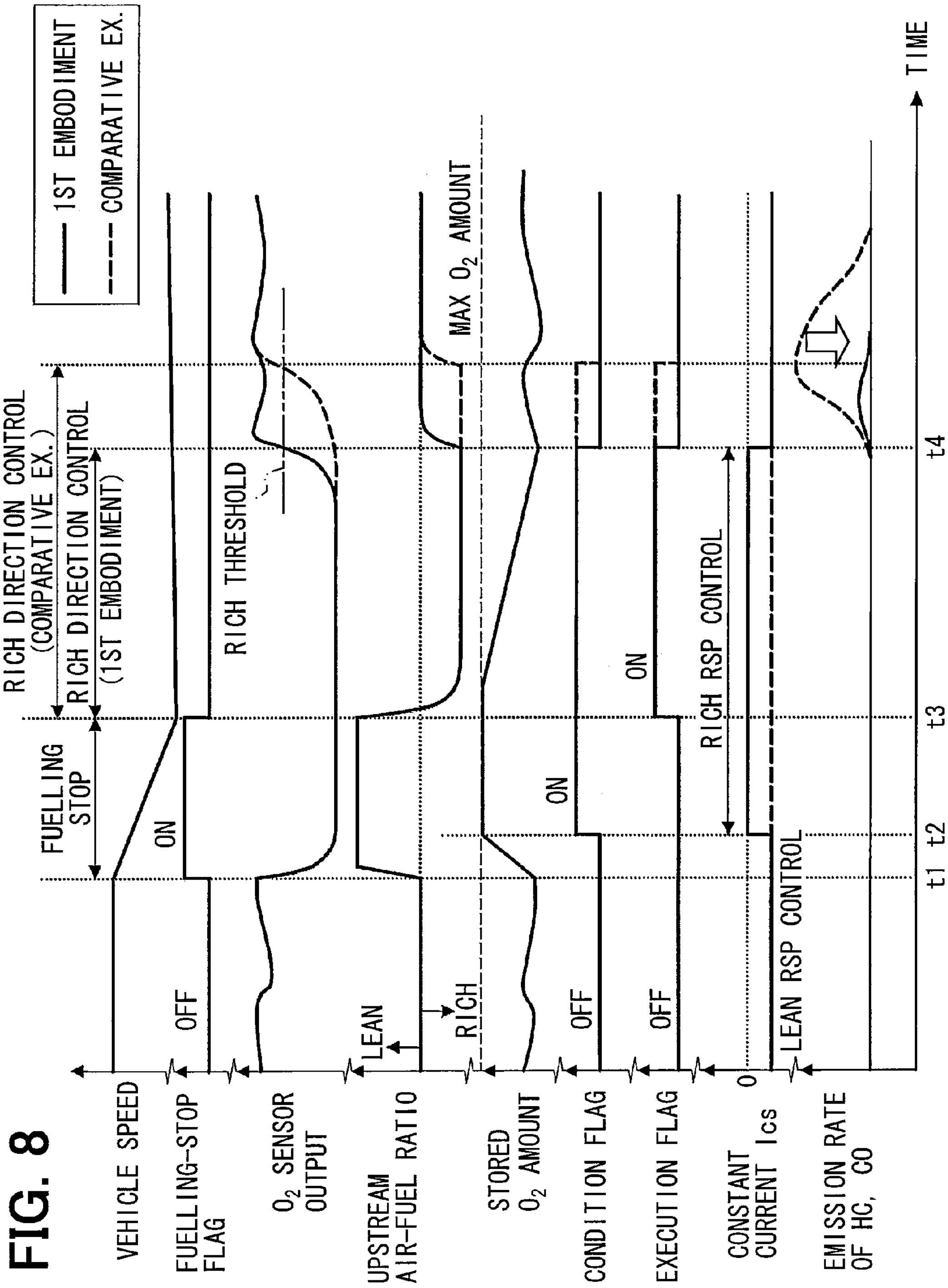
FIG. 8 is a time chart showing changes in vehicle speed, state of a fuelling-stop flag, $O_2$ sensor output, upstream air-fuel ratio, stored $O_2$ amount, state of a condition flag, state of an execution flag, constant current and emission rate of HC and CO, in an emission reduction control according to the first embodiment.
Figure 9:
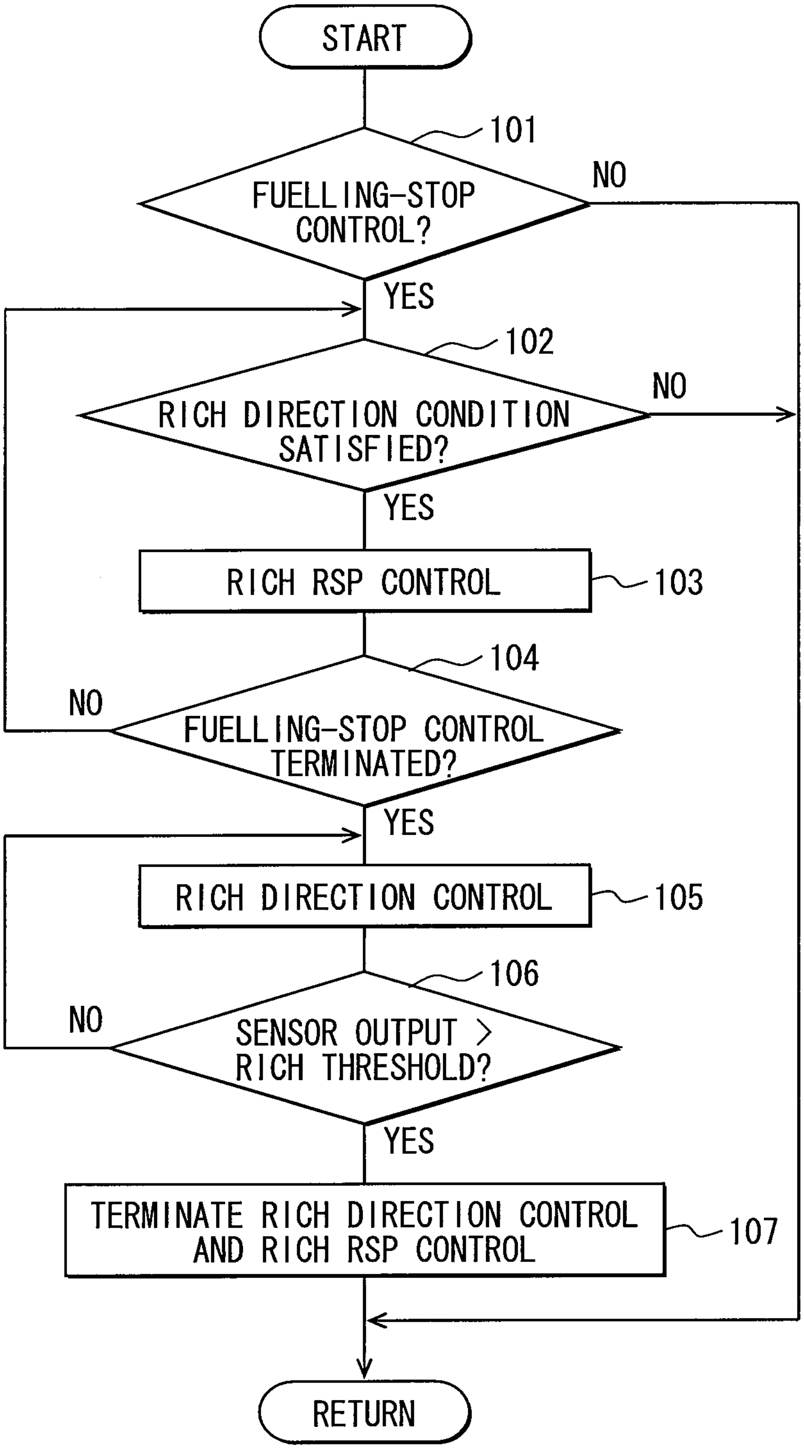
FIG. 9 is a flowchart showing a routine of the emission reduction control according to the first embodiment.

In the first embodiment, the ECU 25 (or the microcomputer 26) executes a routine of an emission reduction control shown in FIG. 9. In the emission reduction control, as shown in FIG. 8, a rich direction control (NOx reduction control) is performed after a fuelling-stop control. In the rich direction control, an air-fuel ratio (upstream air-fuel ratio) of exhaust gas flowing upstream of the upstream catalyst 18 is controlled to become richer (i.e., lower) than the target air-fuel ratio that is set depending on a normal operation condition. In the fuelling-stop control, fuel injection of the engine 11 is stopped. When an output of the oxygen sensor 21 becomes higher than a predetermined rich threshold after a start of the rich direction control, the rich direction control is terminated. Additionally, in the emission reduction control, a rich responsiveness control (rich RSP control) is performed, in which the constant current circuit 27 is controlled so that a rich responsiveness of the oxygen sensor 21 is increased during the rich direction control. The rich responsiveness of the oxygen sensor 21 is the detection responsiveness of the oxygen sensor 21 with respect to rich gas that is exhaust gas having an actual air-fuel ratio richer (i.e., lower) than the stoichiometric air-fuel ratio. Specifically, in the rich RSP control, the constant current circuit 27 is controlled to output the positive constant current (+Ics) such that the exhaust electrode layer 33 supplies oxygen to the atmosphere electrode layer 34.

As shown in FIG. 8, a fuelling-stop flag is turned on at time t1 after a predetermined execution condition of the fuelling-stop control is satisfied during an operation of the engine 11. When the fuelling-stop flag is turned on, the fuelling-stop control is performed to stop fuel injection of the engine 11. Subsequently, at time t3, the execution condition of the fuelling-stop control is not satisfied, and the fuelling-stop flag is turned off so that the fuelling-stop control is terminated. In other words, the fuel injection of the engine 11 is resumed at time t3.

After the termination of the fuelling-stop control, i.e., after the resumption of the fuel injection, the upstream catalyst 18 may become possibly in a lean state, in which a stored oxygen amount (stored $O_2$ amount), i.e., adsorbed oxygen amount in the upstream catalyst 18 is relatively large. In the lean state of the upstream catalyst 18, NOx conversion efficiency of the upstream catalyst 18 may decrease. In order to limit the decrease of the catalytic conversion efficiency due to the lean state of the upstream catalyst 18, in other words, in order to reduce the adsorbed oxygen amount in the upstream catalyst 18, the rich direction control is performed. Specifically, it is determined whether an execution condition (rich direction condition) of the rich direction control is satisfied during the fuelling-stop control. When the rich direction condition is satisfied, a condition flag is turned on at time t2 as shown in FIG. 8. And then, when the fuelling-stop control is finished, an execution flag is turned on at time t3 so that the rich direction control is performed. In the rich direction control, an air-fuel ratio of exhaust gas flowing upstream of the upstream catalyst 18 is controlled to become richer (i.e., lower) than the target air-fuel ratio that is set based on a normal operation condition. Because the air-fuel ratio of exhaust gas flowing into the upstream catalyst 18 can be made to be richer (i.e., lower) in the rich direction control, it can be limited that the upstream catalyst 18 becomes in the lean state. In other words, the stored oxygen amount in the upstream catalyst 18 can be reduced.

After the start of the rich direction control, an output of the oxygen sensor 21 exceeds the predetermined rich threshold at time t4. The predetermined rich threshold corresponds, for example, to the stoichiometric air-fuel ratio or richer a little. At time t4, it is determined that the limitation of the lean state of the upstream catalyst 18 is finished, so that the rich direction control is terminated.

On the other hand, in a comparative example shown by thick dash lines in FIG. 8, the lean RSP control is continued to be performed during the rich direction control without performing the rich RSP control. Because the rich responsiveness of the oxygen sensor 21 is relatively low in the lean RSP control, a time point at which the output of the oxygen sensor 21 exceeds the predetermined rich threshold (i.e., a time point at which the limitation of the lean state of the upstream catalyst 18 is finished) retards in the comparative example. Hence, a time point of the termination of the rich direction control retards, and an emission rate of CO or HC (rich component) generated in the rich direction control may thereby increase. As a result, emission gas may be deteriorated in the comparative example.

In the first embodiment, as shown by thick solid line in FIG. 8, the rich direction condition is satisfied during the fuelling-stop control, and the condition flag is turned on at time t2. Accordingly, the rich RSP control is performed at time t2 to control the constant current circuit 27 so that the rich responsiveness of the oxygen sensor 21 is increased. For example, the constant current circuit 27 may be controlled to stop applying the constant current Ics, in other words, the constant current Ics may be set at zero. Alternatively, the constant current circuit 27 may be controlled to change a flow direction of the constant current Ics such that the rich sensitivity of the oxygen sensor 21 is increased to enhance the rich responsiveness of the oxygen sensor 21. In other words, in a case where the lean RSP control is performed before a start of the rich RSP control, the rich responsiveness of the oxygen sensor 21 can be increased in the rich RSP control, for example, by stopping applying the constant current Ics (i.e., setting the constant current Ics at zero) or by changing the flow direction of the constant current Ics such that the rich responsiveness of the oxygen sensor 21 is increased.

Accordingly, it can be prevented that the time point, at which the output of the oxygen sensor 21 exceeds the predetermined rich threshold after the start of the rich direction control, retards. In other words, it can be prevented that the time point, at which the limitation of the lean state of the upstream catalyst 18 is determined to be finished, retards. Thus, the rich direction control can be terminated relatively early. As a result, the emission rate of CO or HC (rich component) generated in the rich direction control after the fuelling-stop control can be more reduced in the present embodiment than in the comparative example as shown in FIG. 8, and the deterioration of the emission gas can be limited.

The routine of the emission reduction control executed by the ECU 25 (or the microcomputer 26) will be described with reference to FIG. 9.

The routine of the emission reduction control shown in FIG. 9 is repeatedly executed in a predetermined period in a state where the ECU 25 is turned on, and may be used as an example of a rich direction control portion and an characteristic control portion. When the emission reduction control is started, it is determined firstly at step 101 whether the fuelling-stop control is performed. When the fuelling-stop control is determined not to be performed at step 101, the routine of the emission reduction control is terminated without performing any other control operations.

When the fuelling-stop control is determined to be performed at step 101, it is determined at step 102 whether the rich direction condition is satisfied. Here, the rich direction condition includes conditions (1) to (3) shown as follows.

(1) Warm-up of the upstream catalyst 18 is finished.

(2) The stored oxygen amount (detection value or estimate value) in the upstream catalyst 18 is equal to or higher than a predetermined value, or the fuelling-stop control is performed for a predetermined time period or more.

(3) A request to stop the engine 11 is not provided.

When the above-described all conditions (1) to (3) are satisfied, the rich direction condition is satisfied. However, when either one of the above-described conditions (1) to (3) is not satisfied, the rich direction condition is not satisfied.

When the rich direction condition is determined not to be satisfied at step 102, the routine of the emission reduction control is terminated without performing any control operations.

When the rich direction condition is determined to be satisfied at step 102, the condition flag is turned on, and a control operation of step 103 is performed. At step 103, the rich RSP control is performed to control the constant current circuit 27 such that the rich responsiveness of the oxygen sensor 21 is increased. For example, the constant current circuit 27 is controlled to be stopped applying the constant current Ics (i.e., the constant current circuit 27 is controlled to set the constant current Ics at zero). Alternatively, the constant current circuit 27 may be controlled to change the flow direction of the constant current Ics so as to increase the rich responsiveness of the oxygen sensor 21. In this case, the constant current circuit 27 is controlled to apply the constant current (positive constant current +Ics) such that oxygen is supplied from the exhaust electrode layer 33 to the atmosphere electrode layer 34.

After the control operation of step 103, it is determined at step 104 whether the fuelling-stop control is terminated. When the fuelling-stop control is determined not to be terminated at step 104, the control operation of step 102 is performed. When the fuelling-stop control is determined to be terminated at step 104 (i.e., when the fuel injection is resumed), a control operation of step 105 is performed. At step 105, the execution flag is turned on, and the rich direction control is performed, in which the air-fuel ratio (upstream air-fuel ratio) of exhaust gas flowing upstream of the upstream catalyst 18 is controlled to become richer (i.e., lower) than the target air-fuel ratio that is set based on the normal operation condition. Because the air-fuel ratio of exhaust gas flowing into the upstream catalyst 18 can be made to be richer (i.e., lower) in the rich direction control, it can be limited that the upstream catalyst 18 becomes in the lean state. In other words, the stored oxygen amount in the upstream catalyst 18 can be reduced.

At next step 106, it is determined whether the output of the oxygen sensor 21 exceeds the predetermined rich threshold that is, for example, a value corresponding to the stoichiometric air-fuel ratio or richer a little. When the output of the oxygen sensor 21 is determined to be equal to or lower than the predetermined rich threshold at step 106, the control operation of step 104 is performed. When the output of the oxygen sensor 21 is determined to be higher than the predetermined rich threshold at step 106, a control operation of step 107 is performed. At step 107, the rich direction control and the rich RSP control are terminated. In other words, the lean RSP control is performed, in which the constant current circuit 27 is controlled to change the flow direction of the constant current Ics so that the lean responsiveness of the oxygen sensor 21 is increased. A control portion of the ECU 25 (microcomputer 26) which performs the control operation of step 105 may be used as an example of the rich direction control portion that performs the rich direction control after a termination of the fuelling-stop control. A control portion of the ECU 25 (microcomputer 26) which performs the control operation of step 103 may be used as an example of a characteristic control portion that performs the rich RSP control during the rich direction control.

In the above-described first embodiment, the constant current circuit 27 provided outside the oxygen sensor 21 applies the constant current Ics between the pair of sensor electrodes 33 and 34. Accordingly, the output characteristic of the oxygen sensor 21 can be changed, and the rich responsiveness or the lean responsiveness of the oxygen sensor 21 can be increased. Furthermore, there is no need to incorporate an auxiliary electrochemical cell or the like to an inside of the oxygen sensor 21. Therefore, the output characteristic of the oxygen sensor 21 can be changed without great design changes and cost increase.

In the emission control system 1, as described above, the rich direction control is continued to be performed after a termination of the fuel-stopping control until the output of the oxygen sensor 21 exceeds the predetermined rich threshold. The rich RSP control can be performed in the emission control system 1, and the constant current circuit 27 is controlled in the rich RSP control to increase the rich responsiveness of the oxygen sensor 21 during the rich direction control. Accordingly, the time point at which the output of the oxygen sensor 21 exceeds the predetermined rich threshold after the start of the rich direction control (i.e., the time point at which the limitation of the lean state of the upstream catalyst 18 is determined to be finished) can be prevented from retarding. Hence, the time point of the termination to the rich direction control can be made to be early relatively. As a result, the emission rate of CO or HC (rich component) generated in the rich direction control after the fuelling-stop control can be reduced, and the deterioration of the emission gas can be limited.

In the first embodiment, the rich RSP control is started at a time point at which the rich direction condition is satisfied during the fuelling-stop control. Therefore, the rich RSP control can be started before the rich direction control is started.

(Second Embodiment)

A second embodiment will be described referring to FIG. 10. Explanations of parts in the second embodiment that are substantially same as parts in the first embodiment are omitted or simplified, and parts different from the first embodiment will be mainly described in the second embodiment.

In the first embodiment, the rich RSP control is started when the execution condition (rich direction condition) of the rich direction control is satisfied during the fuelling-stop control. In the second embodiment, an ECU 25 (or a microcomputer 26) executes a routine of an emission reduction control shown in FIG. 10, and the rich RSP control is started in an early period after the rich direction control is started.

Figure 10:
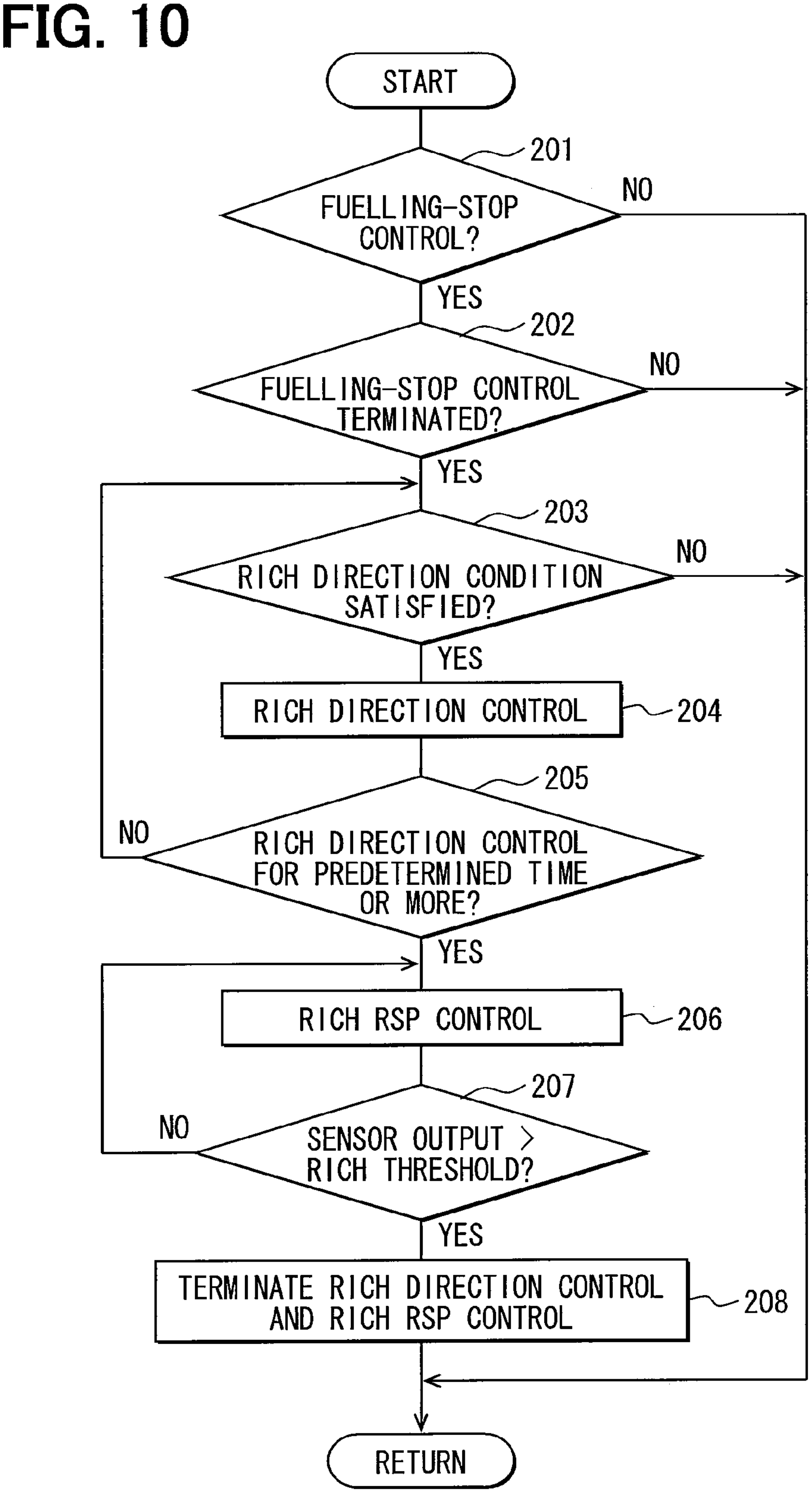
FIG. 10 is a flowchart showing a routine of an emission reduction control according to a second embodiment of the present disclosure.

In the routine of the emission reduction control shown in FIG. 10, it is determined firstly at step 201 whether the fuelling-stop control is performed. When the fuelling-stop control is determined to be performed at step 201, it is determined at step 202 whether the fuelling-stop control is terminated. When the fuelling-stop control is determined to be terminated at step 202, in other words, when fuel injection of an engine 11 is determined to be resumed, it is determined at step 203 whether an execution condition (rich direction condition) of the rich direction control is satisfied. The rich direction condition of the second embodiment is same as the rich direction condition of the first embodiment described in the explanation of step 102 shown in FIG. 9.

When the rich direction condition is determined to be satisfied at step 203, the rich direction control is performed at step 204. In the rich direction control, an air-fuel ratio of exhaust gas flowing into an upstream catalyst 18 is made to be richer (lower). Accordingly, it can be limited that the upstream catalyst 18 becomes in a lean state, in other words, a stored oxygen amount in the upstream catalyst 18 can be reduced.

At next step 205, it is determined whether the rich direction control is performed for a predetermined time period or more. When the rich direction control is determined not to be performed for the predetermined time period or more, the control operation of step 203 is performed. When the rich direction control is determined to be performed for the predetermined time period or more, the rich RSP control is performed at step 206. Specifically, in the rich RSP control, the constant current circuit 27 is controlled to stop applying a constant current Ics. Alternatively, the constant current circuit 27 may be controlled to change a flow direction of a constant current Ics so that a rich responsiveness of the oxygen sensor 21 is increased.

At next step 207, it is determined whether an output of the oxygen sensor 21 exceeds a predetermined rich threshold. When the output of the oxygen sensor 21 is determined to be equal to or lower than the predetermined rich threshold, the control operation of step 206 is performed. When the output of the oxygen sensor 21 is determined to be higher than the predetermined rich threshold at step 206, the rich direction control and the rich RSP control are terminated at step 208. A control portion of the ECU 25 (microcomputer 26) which performs the control operation of step 204 may be used as an example of the rich direction control portion that performs the rich direction control after a termination of the fuelling-stop control. A control portion of the ECU 25 (microcomputer 26) which performs the control operation of step 206 may be used as an example of a characteristic control portion that performs the rich RSP control during the rich direction control.

In the above-described second embodiment, the rich RSP control is started in the early period after the start of the rich direction control, in other words, the rich RSP control is started after the rich direction control is performed for the predetermined time period or more. Therefore, the rich RSP control can be started after the rich direction control is recognized to be started actually.

(Third Embodiment)

A third embodiment will be described in reference to FIGS. 11 to 13. Explanations of parts in the third embodiment that are substantially same as parts in the first embodiment are omitted or simplified, and parts different from the first embodiment will be mainly described in the third embodiment.

In the first embodiment, the rich direction control is terminated when the output of the oxygen sensor 21 exceeds the predetermined rich threshold after the start of the rich direction control. In the third embodiment, an ECU 25 (or a microcomputer 26) of an emission control system 1 executes a routine of an emission reduction control shown in FIG. 13, and a rich direction control is terminated when an estimate amount (estimate stored oxygen amount) of oxygen stored in an upstream catalyst 18 becomes equal to a predetermined reference threshold (ref. threshold).

Figure 11:
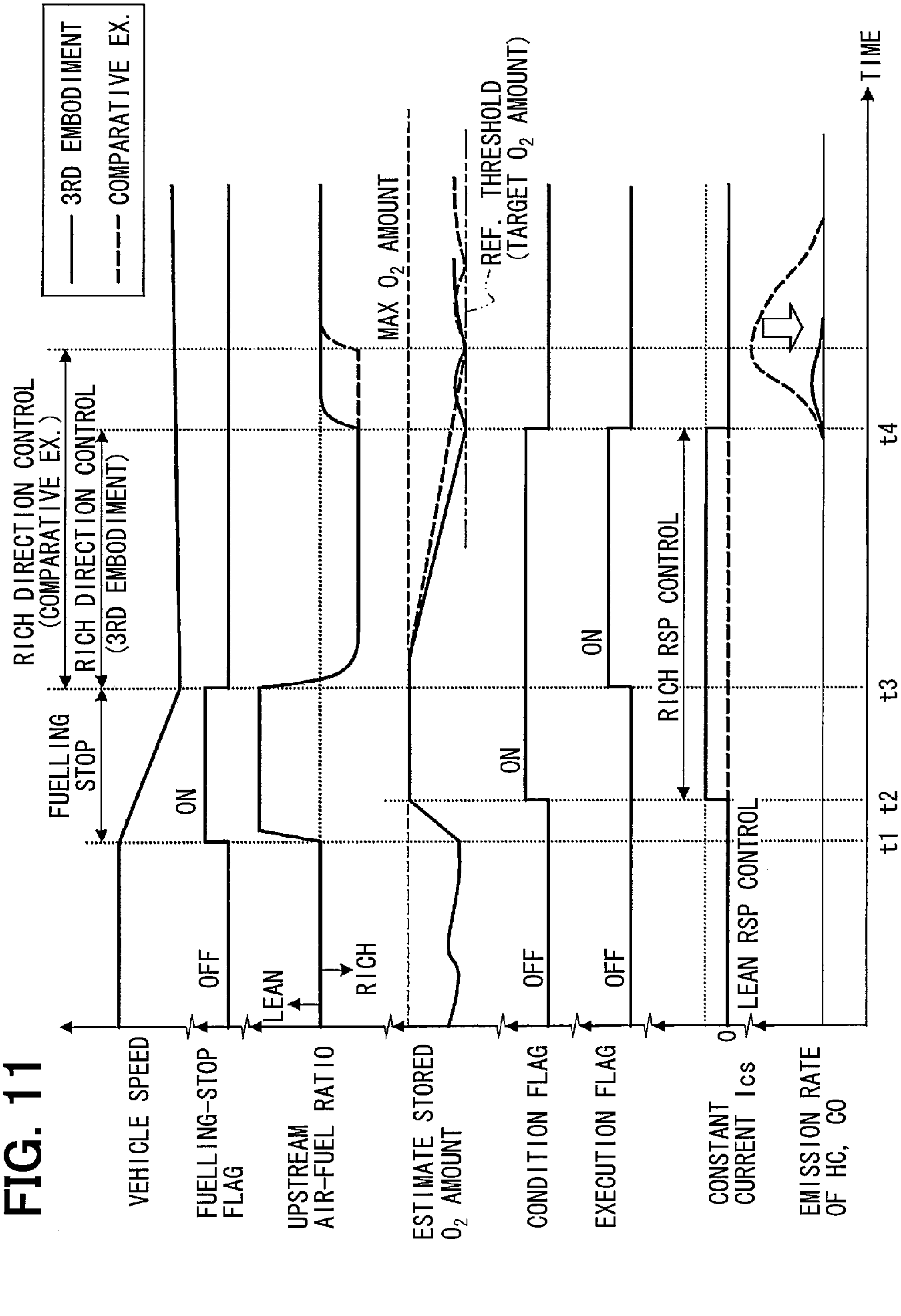
FIG. 11 is a time chart showing changes in vehicle speed, state of a fuelling-stop flag, upstream air-fuel ratio, stored $O_2$ amount, state of a condition flag, state of an execution flag, constant current and emission rate of HC and CO, in an emission reduction control for an emission control system according to a third embodiment of the present disclosure.
Figure 12:
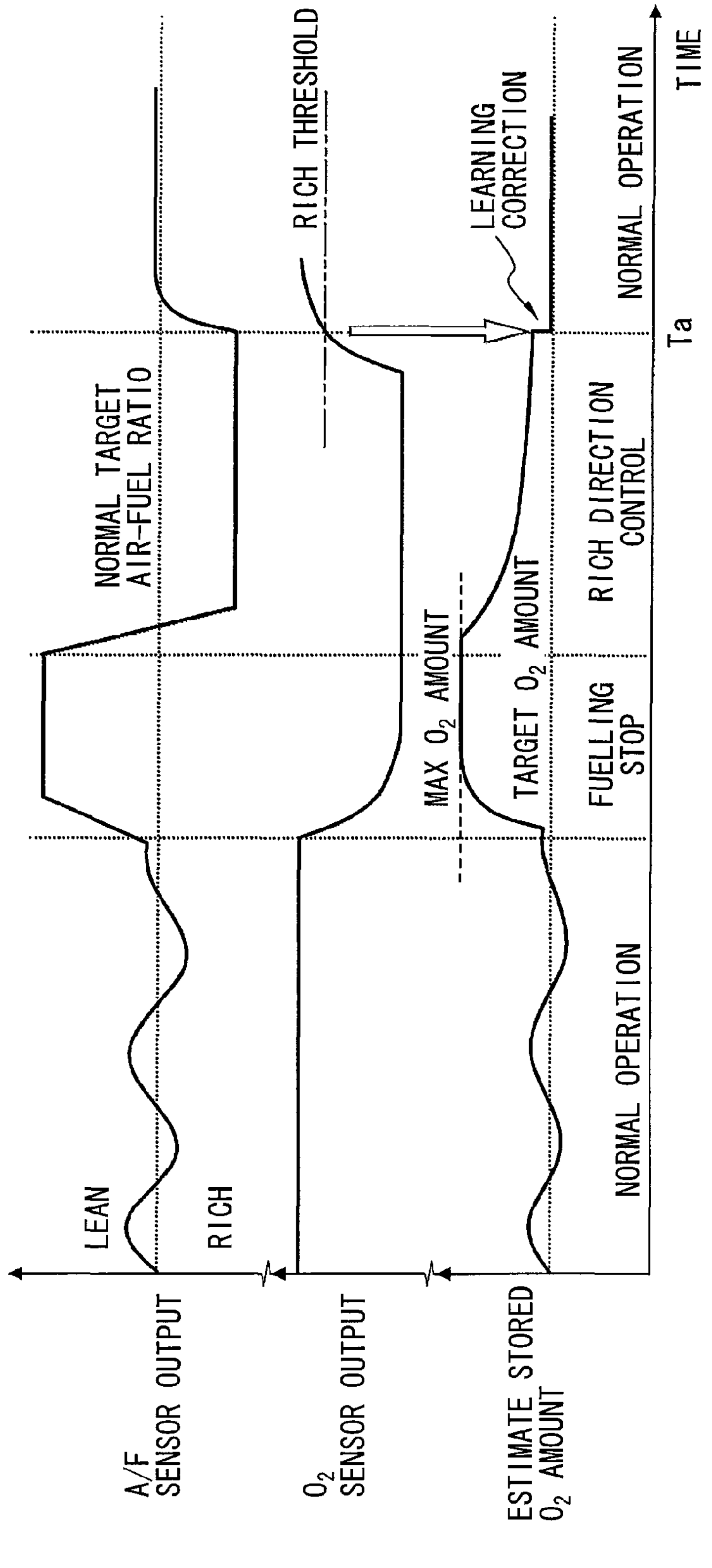
FIG. 12 is a diagram showing an example of a method for estimation of a stored oxygen amount in an upstream catalyst for the emission control system according to the third embodiment.

Specifically, as shown in FIG. 11, a fuelling-stop control is performed at time t1, at which a fuelling-stop flag is turned on due to satisfaction of a predetermined fuelling-stop condition in an operation state of an engine 11. Subsequently, the fuelling-stop control is terminated, and fuel injection of the engine 11 is resumed at time t3, at which the fuelling-stop flag is turned off due to dissatisfaction of the predetermined fuelling-stop condition.

After the termination of the fuelling-stop control, the upstream catalyst 18 may become possibly in a lean state, in which the stored oxygen amount in the upstream catalyst 18 is relatively large. In the lean state of the upstream catalyst 18, catalytic conversion efficiency of the upstream catalyst 18 with respect to NOx may decrease. Thus, by performing the rich direction control, it can be limited that the upstream catalyst 18 becomes in the lean state, in other words, the stored oxygen amount can be reduced. Specifically, it is determined whether an execution condition (rich direction condition) of the rich direction control is satisfied during the fuelling-stop control. When the rich direction condition is satisfied, a condition flag is turned on at time t2 in FIG. 11. And then, when the fuelling-stop control is finished, an execution flag is turned on at time t3 so that the rich direction control is performed.

After the start of the rich direction control, the limitation of the lean state of the upstream catalyst 18 is determined to be finished, and the rich direction control is terminated at time t4, at which the estimate stored oxygen amount (estimate stored $O_2$ amount) in the upstream catalyst 18 becomes equal to the predetermined reference threshold (e.g., target stored oxygen amount (target $O_2$ amount)).

Here, an example of an estimation method of the stored oxygen amount (i.e., calculation method of the estimate stored oxygen amount) in the upstream catalyst 18 will be described with reference to FIG. 12. The estimate stored oxygen amount in the upstream catalyst 18 is calculated by using a map, a mathematical expression or the like based on an output (A/F sensor output) of an A/F sensor 20 (upstream gas sensor), an output ($O_2$ sensor output) of the oxygen sensor 21 (downstream gas sensor), operation conditions of the engine 11 (e.g., an engine rotation speed, an engine load and a coolant temperature), an exhaust-gas temperature and a temperature of the upstream catalyst 18. The map, the mathematical expression and the like used in the calculation of the estimate stored oxygen amount are developed based on test data or design data, and are stored in a ROM or the like of the ECU 25 (or the microcomputer 26).

As shown in FIG. 11, the rich direction control is performed after a termination of the fuelling-stop control, and the output of the oxygen sensor 21 exceeds a predetermined rich threshold at time Ta. At time Ta, an actual stored oxygen amount in the upstream catalyst 18 is determined to decrease and to be the target stored oxygen amount (e.g., from 30 to 40% of a largest stored oxygen amount (max $O_2$ amount)), and the estimate stored oxygen amount is learned and corrected such that the estimate stored oxygen amount at time Ta is used as the target stored oxygen amount. Specifically, a deviation between the estimate stored oxygen amount and the target stored oxygen amount is learned as a correction amount (error), and the estimate stored oxygen amount is corrected by using the learned correction amount.

The learned correction amount is stored in a non-volatile memory such as a backup random access memory (backup RAM), and the stored learned correction amount is used when the estimate stored oxygen amount is calculated. In this case, for example, the estimate stored oxygen amount calculated by using the map, the mathematical expression or the like is corrected with the learned correction amount. Alternatively, the map, the mathematical expression or the like may be corrected with the learned correction amount, and may be used in the calculation of the estimate stored oxygen amount.

In a comparative example (comparative ex.) shown by thick dash lines in FIG. 11, a lean RSP control, in which the constant current Ics is applied so as to increase the lean responsiveness of the oxygen sensor 21, is continued to be performed during the rich direction control without performing the rich RSP control. Because the rich responsiveness of the oxygen sensor 21 is relatively low during the lean RSP control, a time point at which the estimate stored oxygen amount becomes equal to the predetermined reference threshold after the start of the rich direction control (i.e., a time point at which the limitation of the lean state of the upstream catalyst 18 is finished) may retard, and a time point of termination of the rich direction control may retard. Therefore, as shown in FIG. 11, an emission rate of CO or HC (rich component) generated in the rich direction control may be increased. As a result, emission gas may be deteriorated.

In the third embodiment shown by thick solid lines in FIG. 11, the rich RSP control is performed at time t2, at which the condition flag is turned on due to satisfaction of the rich direction condition during the fuelling-stop control. Thus, the time point at which the estimate stored oxygen amount becomes equal to the predetermined reference threshold after the start of the rich direction control (i.e., the time point at which the limitation of the lean state of the upstream catalyst 18 is finished) can be prevented from retarding, and the time point of the termination of the rich direction control can be made to be earlier in the third embodiment than in the comparative example. As a result, the emission rate of CO or HC (rich component) generated in the rich direction control after the termination of the fuelling-stop control can be reduced, and the deterioration of the emission gas can be thereby limited.

Figure 13:
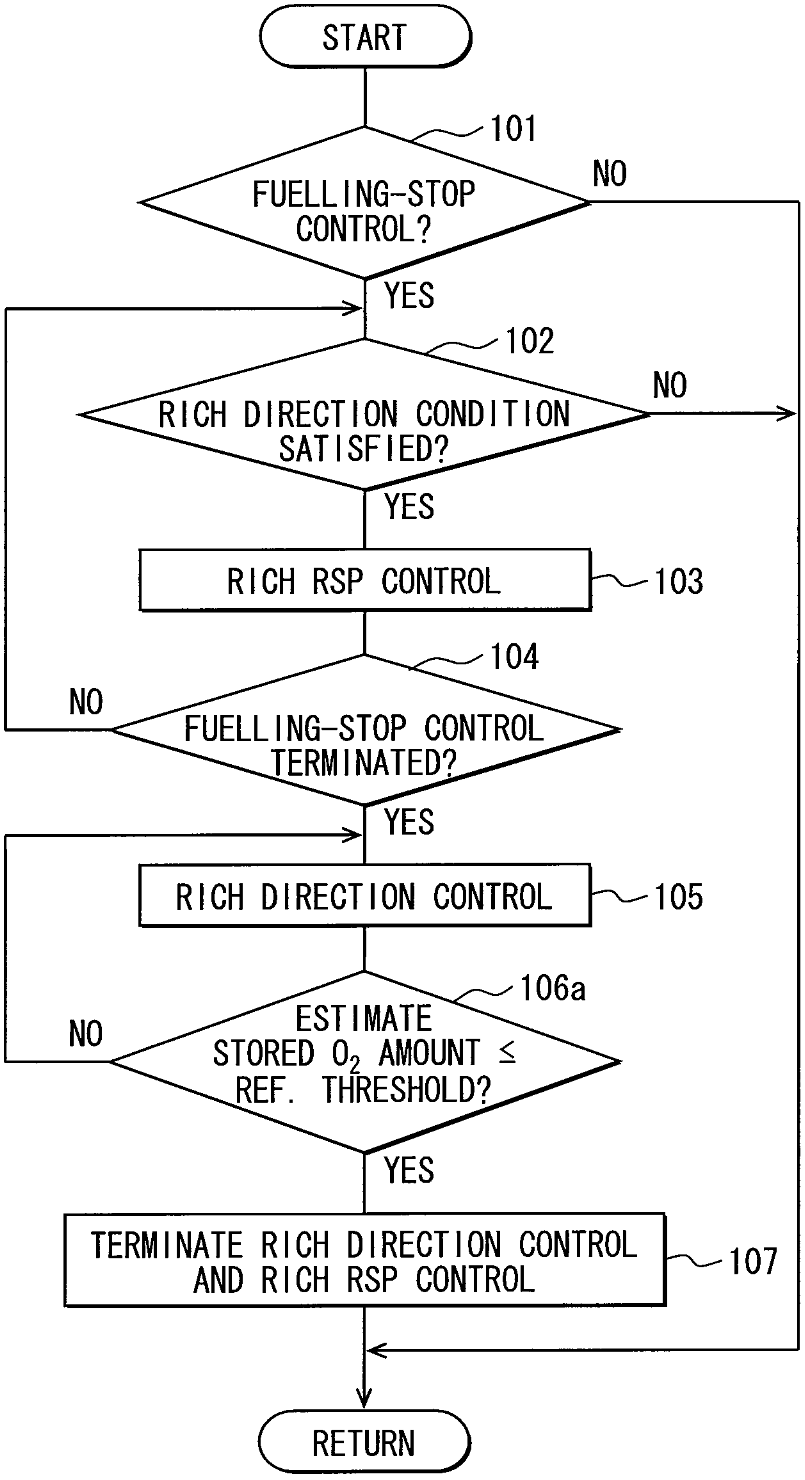
FIG. 13 is a flowchart showing a routine of the emission reduction control according to the third embodiment.

The routine of the emission reduction control of the third embodiment shown in FIG. 13 is same as the routine of the emission reduction control of the first embodiment shown in FIG. 9 except for a control operation of step **106*a*. In other words, the control operation of step 106 of the first embodiment is substituted for the control operation of step 106*a*** in the third embodiment.

In the routine of the emission reduction control shown in FIG. 13, it is determined whether the rich direction condition is satisfied during the fuelling-stop control, and the rich RSP control is performed when the rich direction condition is determined to be satisfied (at steps 101 to 103). Subsequently, it is determined whether the fuelling-stop control is terminated, and the rich direction control is performed when the fuelling-stop control is determined to be terminated, (i.e., the rich direction control is performed when the fuel injection of the engine 11 is determined to be resumed) (at steps 104 and 105).

At next step **106*a*, it is determined whether the estimate stored oxygen amount in the upstream catalyst 18 is equal to or lower than the predetermined reference threshold (ref. threshold). When the estimate stored oxygen amount in the upstream catalyst 18 is determined to be higher than the predetermined reference threshold, the control operation of step 105 is performed. When the estimate stored oxygen amount in the upstream catalyst 18 is determined to be equal to or lower than the predetermined reference threshold, the rich direction control and the rich RSP control are terminated at step 107**.

In the emission control system of the above-described third embodiment, the rich direction control is performed after the termination of the fuelling-stop control until the estimate stored oxygen amount in the upstream catalyst 18 becomes to be the predetermined reference threshold. Additionally, the rich RSP control is performed during the rich direction control. Thus, the time point at which the estimate stored oxygen amount in the upstream catalyst 18 becomes equal to the predetermined reference threshold (i.e., the time point at which the limitation of the lean state of the upstream catalyst 18) can be prevented from retarding, and the time point of the termination of the rich direction control can be made to be earlier. Accordingly, the emission rate of CO or HC (rich component) generated in the rich direction control after the termination of the fuelling-stop control can be reduced, and the deterioration of the emission gas can be thereby limited.

In the above-described third embodiment, the rich RSP control is started to be performed when the rich direction condition is satisfied during the fuelling-stop control. Alternatively, the rich RSP control may be started to be performed in an early period after the start of the rich direction control.

Although the present disclosure has been fully described in connection with the preferred embodiments thereof with reference to the accompanying drawings, it is to be noted that various changes and modifications will become apparent to those skilled in the art.

In the above-described first to third embodiments, the lean RSP control is performed before the start of the rich RSP control, in other words, the constant current circuit 27 applies the constant current Ics so as to increase the lean responsiveness of the oxygen sensor 21 before the start of the rich RSP control. The constant current circuit 27 may stop applying the constant current Ics (i.e., the constant current Ics is equal to zero) before the start of the rich RSP control, and the constant current circuit 27 may apply the constant current Ics so as to increase the rich responsiveness of the oxygen sensor 21 in the rich RSP control.

In the above-described first and second embodiments, the rich RSP control is performed during the rich direction control. Alternatively, the predetermined rich threshold of the output of the oxygen sensor 21 may be set to be leaner (i.e., higher) than the stoichiometric air-fuel ratio without performing the rich RSP control.

In the above-described first to third embodiments, the constant current circuit 27 is connected to the atmosphere electrode layer 34 of the oxygen sensor 21 (sensor element 31). However, for example, the constant current circuit 27 may be connected to the exhaust electrode layer 33 of the oxygen sensor 21 (sensor element 31), or the constant current circuit 27 may be connected to both the atmosphere electrode layer 34 and the exhaust electrode layer 33.

In the above-described first to third embodiments, the present disclosure is applied to the emission control system 1 including the oxygen sensor 21 that has the cup-like shaped sensor element 31. However, for example, the present disclosure may be applied to an emission control system including an oxygen sensor that has a sensor element having a laminated structure.

In the above-described first to third embodiments, the present disclosure is applied to the emission control system 1 in which the oxygen sensor 21 is located downstream of the upstream catalyst 18 in the flow direction of the exhaust gas. However, the present disclosure is not limited to the upstream catalyst 18 or the oxygen sensor 21. The present disclosure may be applied an emission control system in which an exhaust gas sensor, such as an oxygen sensor or an air-fuel ratio sensor, is located downstream of a catalyst for purification of exhaust gas in a flow direction of the exhaust gas.

Additional advantages and modifications will readily occur to those skilled in the art. The disclosure in its broader terms is therefore not limited to the specific details, representative apparatus, and illustrative examples shown and described.

What is claimed is:

1. An emission control system for an internal combustion engine, comprising:

a catalyst used for purification of exhaust gas discharged from the engine;

an exhaust-gas sensor provided downstream of the catalyst in a flow direction of the exhaust gas to detect an air-fuel ratio of the exhaust gas or detect whether the exhaust gas is rich or lean, the exhaust-gas sensor including a sensor element that includes a pair of electrodes and a solid electrolyte body located between the pair of electrodes;

a constant current supply portion that changes an output characteristic of the exhaust-gas sensor by applying a constant current between the pair of electrodes;

a rich direction control portion which performs a rich direction control, in which an air-fuel ratio of the exhaust gas flowing into the catalyst is made to be richer than a target air-fuel ratio set based on a normal operation condition, after a termination of a fuelling-stop control in which fuel injection of the engine is stopped; and a characteristic control portion which performs a rich responsiveness control, in which the constant current supply portion is controlled to increase a detection responsiveness of the exhaust-gas sensor with respect to rich gas, during the rich direction control, wherein one of the pair of electrodes is exposed to the exhaust gas, the other of the pair of electrodes is exposed to air introduced from an atmosphere, and the constant current supply portion applies the constant current flowing from the other of the pair of electrodes to the one of the pair of electrodes to increase the detection responsiveness of the exhaust-gas sensor with respect to the rich gas in the rich responsiveness control.

2. The emission control system according to claim 1, wherein the characteristic control portion controls the constant current supply portion to apply the constant current flowing from the one of the pair of electrodes to the other of the pair of electrodes so as to increase a detection responsiveness of the exhaust-gas sensor with respect to lean gas before a start of the rich responsiveness control.

3. The emission control system according to claim 1, wherein the characteristic control portion starts the rich responsiveness control when an execution condition of the rich direction control is satisfied during the fuelling-stop control.

4. The emission control system according to claim 1, wherein the characteristic control portion starts the rich responsiveness control in an early period after the start of the rich direction control.

5. An emission control system for an internal combustion engine, comprising:

a catalyst used for purification of exhaust gas discharged from the engine;

an exhaust-gas sensor provided downstream of the catalyst in a flow direction of the exhaust gas to detect an air-fuel ratio of the exhaust gas or detect whether the exhaust gas is rich or lean, the exhaust-gas sensor including a sensor element that includes a pair of electrodes and a solid electrolyte body located between the pair of electrodes;

an electronic control unit, including a computer, the electronic control unit being configured to:

change an output characteristic of the exhaust-gas sensor by applying a constant current between the pair of electrodes;

perform a rich direction control, in which an air-fuel ratio of the exhaust gas flowing into the catalyst is made to be richer than a target air-fuel ratio set based on a normal operation condition, after a termination of a fuelling-stop control in which fuel injection of the engine is stopped; and perform a rich responsiveness control, in which the constant current is controlled to increase a detection responsiveness of the exhaust-gas sensor with respect to rich gas, during the rich direction control, wherein one of the pair of electrodes is configured to be exposed to the exhaust gas, the other of the pair of electrodes is configured to be exposed to air introduced from an atmosphere, and the electronic control unit is further configured to apply the constant current flowing from the other of the pair of electrodes to the one of the pair of electrodes to increase the detection responsiveness of the exhaust-gas sensor with respect to the rich gas in the rich responsiveness control.

6. The emission control system according to claim 5, wherein the electronic control unit is further configured to control the constant current to apply the constant current flowing from the one of the pair of electrodes to the other of the pair of electrodes so as to increase a detection responsiveness of the exhaust-gas sensor with respect to lean gas before a start of the rich responsiveness control.

7. The emission control system according to claim 5, wherein the electronic control unit is further configured to start the rich responsiveness control when an execution condition of the rich direction control is satisfied during the fuelling-stop control.

8. The emission control system according to claim 5, wherein the electronic control unit is further configured to start the rich responsiveness control in an early period after the start of the rich direction control.

9. An emission control system for an internal combustion engine, comprising:

a catalyst used for purification of exhaust gas discharged from the engine;

an exhaust-gas sensor provided downstream of the catalyst in a flow direction of the exhaust gas to detect an air-fuel ratio of the exhaust gas or detect whether the exhaust gas is rich or lean, the exhaust-gas sensor including a sensor element that includes a pair of electrodes and a solid electrolyte body located between the pair of electrodes;

a constant current supply portion configured to change an output characteristic of the exhaust-gas sensor by applying a constant current between the pair of electrodes;

a rich direction control portion configured to perform a rich direction control, in which an air-fuel ratio of the exhaust gas flowing into the catalyst is made to be richer than a target air-fuel ratio set based on a normal operation condition, after a termination of a fuelling-stop control in which fuel injection of the engine is stopped; and a characteristic control portion configured to perform a rich responsiveness control, in which the constant current supply portion is controlled to increase a detection responsiveness of the exhaust-gas sensor with respect to rich gas, during the rich direction control, wherein one of the pair of electrodes is exposed to the exhaust gas, the other of the pair of electrodes is exposed to air introduced from an atmosphere, the characteristic control portion is configured to control the constant current supply portion to apply the constant current flowing from the one of the pair of electrodes to the other of the pair of electrodes so as to increase a detection responsiveness of the exhaust-gas sensor with respect to lean gas before a start of the rich responsiveness control, and the constant current supply portion is configured to set the constant current at zero to increase the detection responsiveness of the exhaust-gas sensor with respect to the rich gas in the rich responsiveness control.

* * * * *